US012642917B2

(12) United States Patent
Swanson et al.

(10) Patent No.: US 12,642,917 B2
(45) Date of Patent: Jun. 2, 2026

(54) AUTOINJECTOR AIR REMOVAL APPARATUS AND METHOD OF REMOVING AIR FROM AN AUTOINJECTOR

(71) Applicant: University of Washington, Seattle, WA (US)

(72) Inventors: Shawn Swanson, Seattle, WA (US); Richard Lee, Seattle, WA (US)

(73) Assignee: University of Washington, Seattle, WA (US)

( * ) Notice: Subject to any disclaimer, the term of this patent is extended or adjusted under 35 U.S.C. 154(b) by 920 days.

(21) Appl. No.: 17/758,591

(22) PCT Filed: Jan. 20, 2021

(86) PCT No.: PCT/US2021/014075
§ 371 (c)(1),
(2) Date: Jul. 11, 2022

(87) PCT Pub. No.: WO2021/150539
PCT Pub. Date: Jul. 29, 2021

(65) Prior Publication Data
US 2023/0036869 A1 Feb. 2, 2023

Related U.S. Application Data

(60) Provisional application No. 62/964,577, filed on Jan. 22, 2020.

(51) Int. Cl.
| *A61M 5/36* | (2006.01) |
| *A61M 5/19* | (2006.01) |
| *A61M 5/20* | (2006.01) |
| *A61M 5/31* | (2006.01) |

(52) U.S. Cl.
CPC ................ *A61M 5/36* (2013.01); *A61M 5/19* (2013.01); *A61M 5/2046* (2013.01); *A61M 2005/3128* (2013.01)

(58) Field of Classification Search
CPC ........ A61M 5/36; A61M 5/19; A61M 5/2046; A61M 2005/3128
See application file for complete search history.

(56) References Cited

U.S. PATENT DOCUMENTS

| 3,892,237 A | 7/1975 | Steiner |
| 4,177,149 A | 12/1979 | Rosenberg |
| 5,599,312 A | 2/1997 | Higashikawa |

(Continued)

OTHER PUBLICATIONS

Written Opinion and International Search Report for corresponding PCT application No. PCT/US2021/014075, dated Mar. 17, 2021.

(Continued)

*Primary Examiner* — Edelmira Bosques
(74) *Attorney, Agent, or Firm* — McDonell Boehnen Hulbert & Berghoff LLP

(57) ABSTRACT

An air removal apparatus for an autoinjector is disclosed. The air removal apparatus can remove or trap air within the autoinjector, preventing the removed or trapped air from displacing medicament or being injected into the patient. The air removal apparatus removes or traps air by creating a vacuum. The vacuum can remove air from the medicament and can trap air within a section of the auto injector that is separated from the medicament.

8 Claims, 9 Drawing Sheets

(56) References Cited

U.S. PATENT DOCUMENTS

| | | | | |
|---|---|---|---|---|
| 6,391,003 | B1 * | 5/2002 | Lesch, Jr. ............. | A61M 5/326 604/110 |
| 9,555,197 | B2 | 1/2017 | Huwiler | |
| 2008/0264261 | A1 | 10/2008 | Kavazov | |
| 2011/0224612 | A1 * | 9/2011 | Lum ....................... | A61M 5/36 141/2 |
| 2012/0029471 | A1 | 2/2012 | Lee | |
| 2014/0039456 | A1 | 2/2014 | Ocuject | |
| 2017/0290986 | A1 | 10/2017 | Chan | |

OTHER PUBLICATIONS

"Diba Omnifit® High Flow Bubble Trap, PVC, 10 μm PTFE filter; 1/ea" Cole-Parmer Instrument Company LLC, https://www.coleparmer.com/i/diba-omnifit-high-flow-bubble-trap-pvc-10-m-ptfe-filter-1-ea/ 2194039, retrieved Dec. 1, 2022.

* cited by examiner

_300_

_302_

REMOVING AIR FROM A SUBSTANCE TO BE INJECTED BY PASSING THE AIR THROUGH A MATERIAL THAT IS AT LEAST ONE OF POROUS AND HYDROPHOBIC

_304_

DELIVERING THE SUBSTANCE TO A PATIENT

400

TRIGGERING AN INJECTION FOR A SUBSTANCE    402

REMOVING AIR FROM THE SUBSTANCE    404

DELIVERING THE SUBSTANCE TO A PATIENT    406

AUTOINJECTOR AIR REMOVAL APPARATUS AND METHOD OF REMOVING AIR FROM AN AUTOINJECTOR

CROSS REFERENCE TO RELATED APPLICATION

This application is a U.S. National Phase application of, and claims the benefit of, International (PCT) Application No. PCT/US21/14075, filed Jan. 20, 2021, which claims priority to U.S. Provisional Application No. 62/964,577 filed Jan. 22, 2022, the contents of both of which are hereby incorporated by reference in their entirety.

FILED OF THE DISCLOSURE

The present disclosure relates to an apparatus and method for injecting medicaments into a patient. More specifically, the present disclosure relates to an autoinjector that can remove air or gas from a medicament before injection.

BACKGROUND

Autoinjectors involve a needle injection apparatus that can deliver a specific dose of a medicament to a patient. Autoinjectors can deliver the medicament to a patient through a mostly automated process. Because the injection process is mostly automated, autoinjectors can be easy to use and can be operated by the patients receiving the medicament.

SUMMARY

Various non-limiting aspects of the present disclosure will now be provided to illustrate features of the disclosed apparatus, methods, and compositions. Examples of apparatus, methods, and compositions for endodontic treatments are provided.

In one embodiment, an autoinjector is disclosed. The autoinjector includes a first chamber configured to hold a substance, the first chamber including a base. The autoinjector also includes a second chamber that is coupled to the first chamber, the second chamber is defined by the base of the first chamber, a first wall, and a plunger, the second chamber is configured to increase in volume in response to the plunger moving away from the base of the first chamber. The autoinjector also includes a hole disposed through the base of the first chamber such that the hole is in fluid communication with the first chamber and the second chamber. The first wall has a gas-permeable portion. Increasing the volume of the second chamber draws the substance from the first chamber into the second chamber and expels a gas out of the second chamber and through the gas-permeable portion.

In certain implementations, the autoinjector can further include an arm that includes a first end and a second end opposite the first end, the arm is coupled to the first chamber at the first end and the second chamber at the second end such that the arm forms an airtight seal between the arm and the first chamber and the second chamber, the arm is configured to move with the plunger.

In certain implementations, the autoinjector can further include a third chamber, the third chamber is defined by the space between the arm, the first chamber, and the second chamber, the third chamber is configured to increase in volume in response to the plunger moving away from the base of the first chamber.

In certain implementations, increasing the volume of the third chamber can create a vacuum within the third chamber.

In certain implementations, the autoinjector can further include a needle coupled to the plunger such that the needle is in fluid communication with the second chamber.

In certain implementations, the second chamber can be narrower than the first chamber.

In certain implementations, the hole can be a one-way valve.

In certain implementations, the first chamber and second chamber can be concentric.

In certain implementations, the second chamber can be cylindrical.

In one embodiment, an autoinjector is disclosed. The autoinjector includes a first chamber configured to hold a substance, the first chamber including a base. The autoinjector also includes a second chamber coupled to the first chamber, the second chamber is defined by the base of the first chamber, a first wall, and a plunger, the second chamber is configured to increase in volume in response to the plunger moving away from the base of the first chamber. The autoinjector also includes a hole disposed through the base of the first chamber such that the hole is in fluid communication with the first chamber and the second chamber. The autoinjector also includes an arm including a first end and a second end opposite the first end, the arm is coupled to the first chamber at the first end and the second chamber at the second end such that the arm forms an airtight seal between the arm and the first chamber and the second chamber, the arm is configured to move with the plunger. The first wall has a gas-permeable portion. Increasing the volume of the second chamber draws the substance from the first chamber into the second chamber and forms a vacuum between the arm and the second chamber.

In certain implementations, the vacuum can be formed in a third chamber, and the third chamber is defined by a space between the arm, the first chamber, and the second chamber.

In certain implementations, the third chamber can be configured to increase in volume in response to the plunger moving away from the base of the first chamber.

In certain implementations, the vacuum can draw gas out of the second chamber through the gas-permeable portion.

In certain implementations, the second chamber can be narrower than the first chamber. In certain implementations, the arm can be directly connected to the plunger.

In certain implementations, the autoinjector can further include a needle coupled to the plunger such that the needle is in fluid communication with the second chamber.

In certain implementations, the hole can be a one-way valve.

In certain implementations, the first chamber and second chamber can be concentric.

In certain implementations, the second chamber can be cylindrical.

In certain implementations, the substance can be a liquid, and the gas is removed from within the liquid via a material that is at least one of porous and hydrophobic, and the material is configured to de-bubble the liquid.

In one embodiment, a method of removing a gas from an autoinjector is disclosed. The method of removing a gas from an autoinjector includes (i) forming an airtight seal on an exterior of a chamber with an arm, (ii) expanding the chamber, (iii) drawing a substance into the chamber, and (iv) creating a vacuum between the chamber and the arm to remove the gas from the chamber.

In one embodiment, another method of removing a gas from an autoinjector is disclosed. The method of removing a gas from an autoinjector includes (i) removing air from a substance to be injected by passing the air through a material that is at least one of porous and hydrophobic, and (ii) delivering the substance to a patient.

In one embodiment, a method of removing a gas from an autoinjector is disclosed. The method of removing gas from an autoinjector includes (i) triggering an injection for a substance, (ii) removing air from the substance, and (iii) delivering the substance to a patient.

Figure 1:
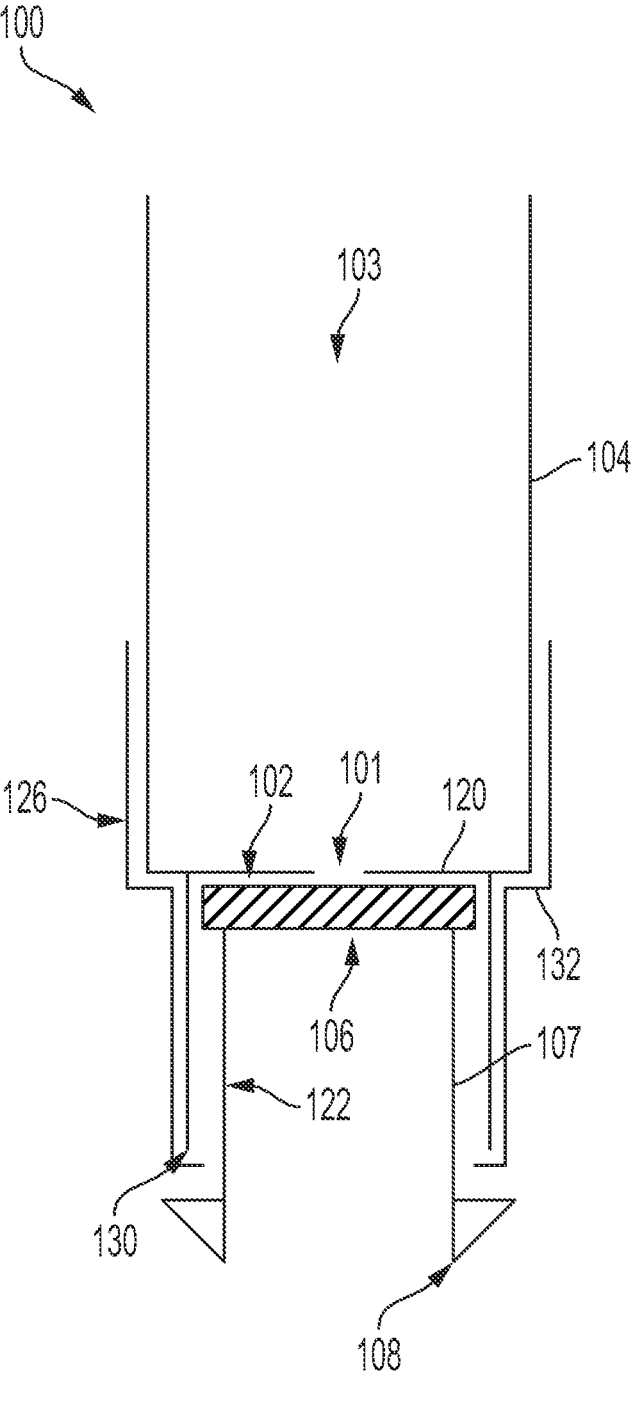
FIG. 1 is a side cross-sectional view schematically illustrating an example air removal apparatus of an autoinjector.

Throughout the drawings, reference numerals may be re-used to indicate a general correspondence between referenced elements. The drawings are provided to illustrate example embodiments described herein and are not intended to limit the scope of the disclosure.

DETAILED DESCRIPTION

When administering a medicament to a patient through an injection, medical professionals try to prevent gas from being injected into the patient. If gas is injected into the patient, that gas can cause several problems. For example, the injected gas may cause an air embolism or may cause an incorrect dose of medicament to be delivered to the patient. Even if the gas is not injected into the patient, the gas may displace the medicament within the syringe, resulting in the patient receiving an incorrect dose.

The above-stated problems of injecting gas and the gas displacing a medicament also exist with an autoinjector. Many autoinjectors come prefilled with a specific dose of a medicament. Because the injection process is mostly automated, many autoinjectors do not allow the operator to control or adjust the dose that is delivered to the patient. Thus, the operator and patient typically depend on the autoinjector to deliver the correct dose. Because the operator and patient depend on the autoinjector to operate correctly, they may have no way of knowing if the patient received the correct dose. If any amount of gas gets injected in the patient during the autoinjection process, or if the gas displaces the medicament within the autoinjector, the patient could receive the incorrect dose of medicament, which could lead to severe consequences for the patient.

An autoinjector that can remove or trap any air or gas from the medicament for administration can prevent these types of severe consequences from occurring. By removing any air or gas from the medicament for administration, the autoinjector can more reliably deliver the correct dose of medicament to the patient. Additionally, removing air from the medicament for administration can prevent any other complications that are caused by injecting air into a patient. Furthermore, an autoinjector that can remove air from the medicament for administration in an automated manner ensures that the air removal process does not hinder the injection process.

Accordingly, the following disclosure provides methods and systems for addressing the above potential issues. In particular, in some embodiments, an autoinjector is provided and configured such that gas from within a liquid in the autoinjector is removed using a porous and/or hydrophobic material configured to de-bubble the liquid. In some embodiments, an autoinjector system for liquid and gas is provided. The gas is removed from the liquid by de-bubbling and thus preparing the liquid for injection. In some embodiments, an autoinjector system for liquid and gas (with the gas removed) is provided. The gas is removed from the liquid using a porous, hydrophobic material, thereby de-bubbling and thus preparing the liquid for injection. In some embodiments, an injection system is provided, wherein the injection system includes a porous and/or hydrophobic membrane. In some embodiments, an injection system is provided, wherein the injection system includes a porous and/or hydrophobic membrane, and wherein a vacuum source is provided on one side of the membrane and a liquid to be injected (which may include air, including any general gas) is on the other side of the membrane.

With reference to the figures, FIGS. 1-6 depict an air removal apparatus 100 for an autoinjector. As will be further described below, the air removal apparatus 100 is configured to remove or trap air within the autoinjector, thereby preventing that air from displacing medicament or from being injected into a patient. Once the air is removed or trapped, the autoinjector can deliver medicament to the patient. In some embodiments, the air removal apparatus 100 removes or traps air by creating a vacuum. The vacuum can remove air from the medicament and can trap air within a section of the autoinjector that is separated from the medicament. As such, the vacuum allows for the autoinjector to remove or trap any air within the closed system without the need for external equipment.

Figure 3:
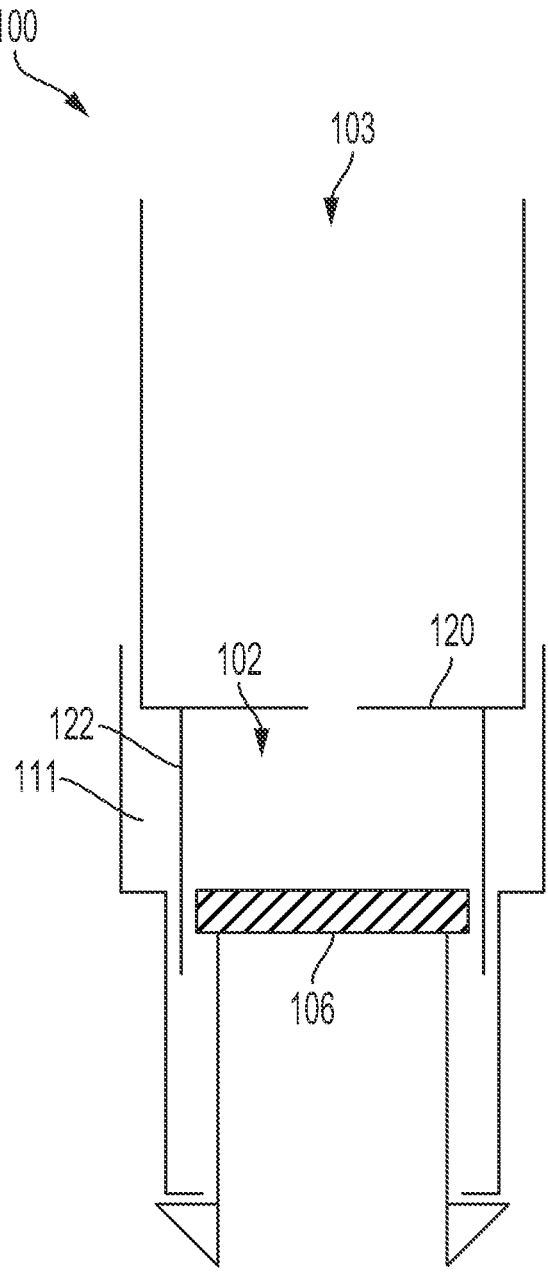
FIG. 3 is a side cross-sectional view schematically illustrating an example air removal apparatus of an autoinjector after an injection has been initiated.
Figure 4:
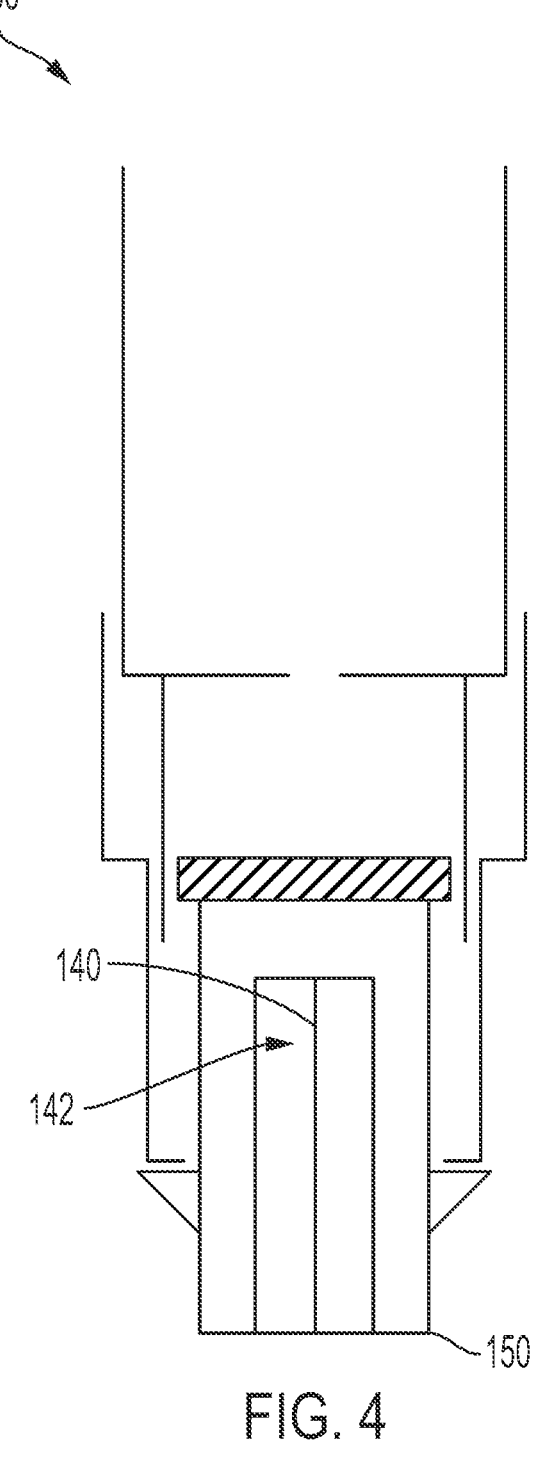
FIG. 4 is a side cross-sectional view schematically illustrating an example air removal apparatus of an autoinjector after an injection has been initiated.
Figure 5:
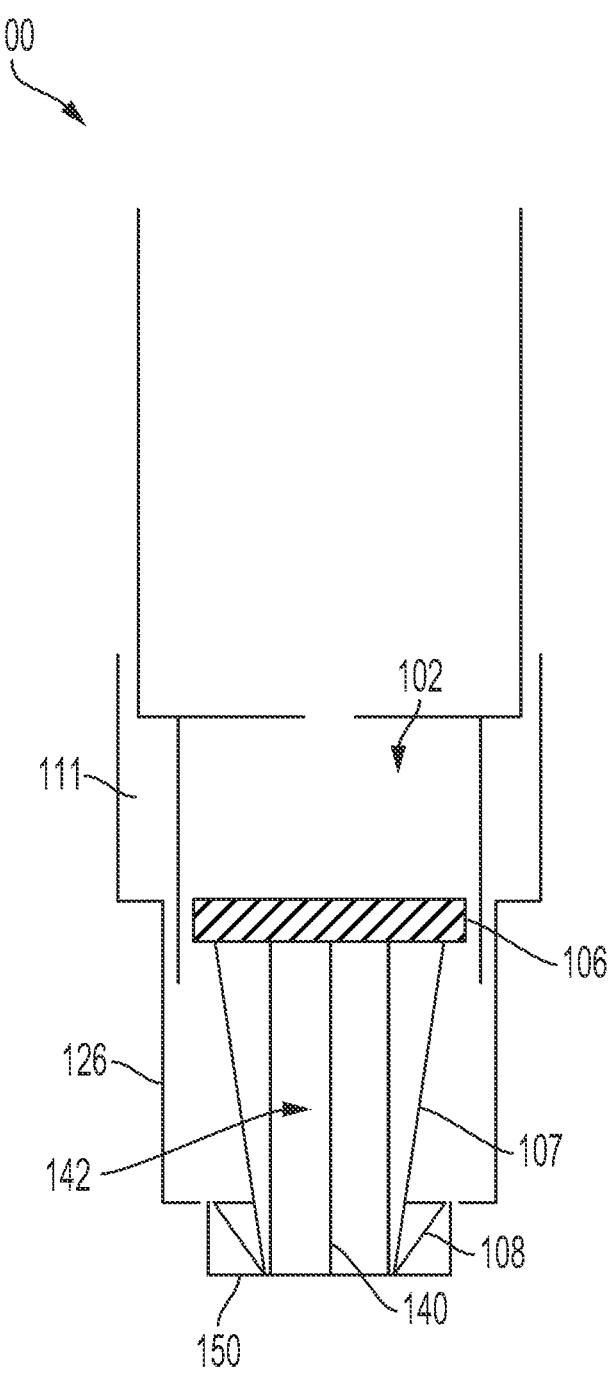
FIG. 5 is a side cross-sectional view schematically illustrating an example air removal apparatus of an autoinjector after an injection has been initiated.
Figure 6:
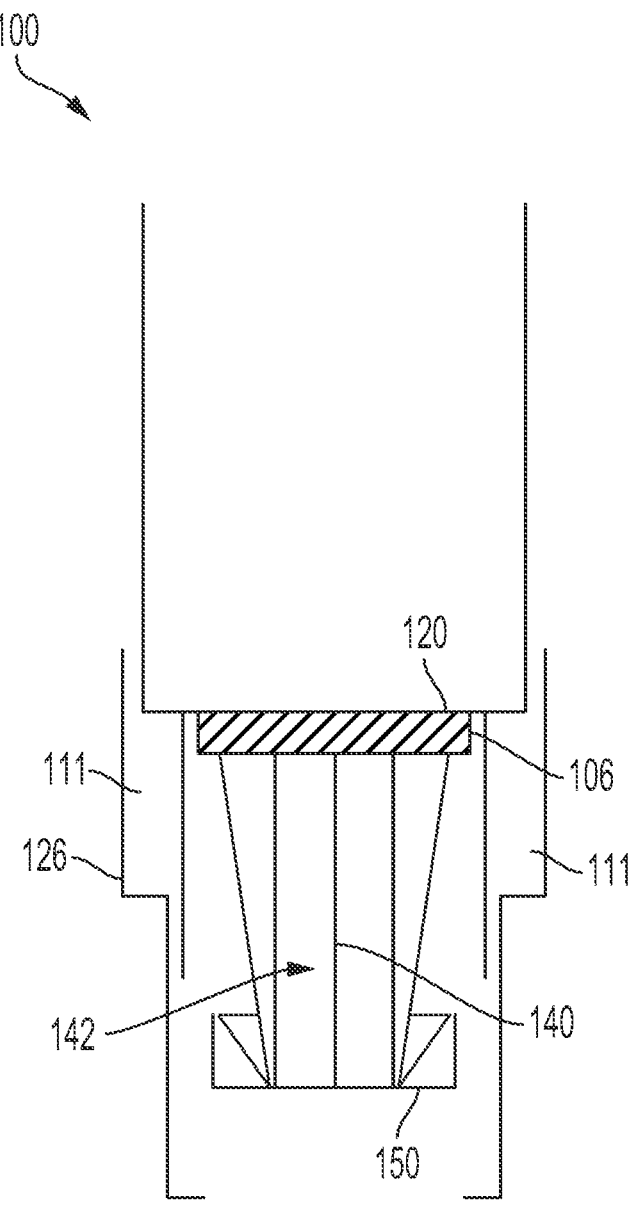
FIG. 6 is a side cross-sectional view schematically illustrating an example air removal apparatus of an autoinjector after an injection been delivered.

As illustrated in FIGS. 1-6, the air removal apparatus 100 can include several components. In particular, as shown in FIG. 1, the air removal apparatus 100 includes a first chamber 103 that has a base 120 with a hole 101 disposed through the base 120, a plunger 106, a second chamber 102 positioned between the base 120 and the plunger 106, and a first wall 122, and. In a further implementation, as shown in FIGS. 5-6, the air removal apparatus 100 may include an arm 126. In various implementations the first chamber 103 may be a first chamber 103, the second chamber 102 may be a second chamber 102, the first wall 122 may be a second chamber wall 122, and the arm 126 may be an air chamber arm 126. In one specific implementation, the air removal apparatus 100 can include a hole 101, a second chamber 102, a first chamber 103, a first chamber wall 104, a plunger 106, a plunger arm 107, a plunger arm end 108, an air chamber 111, a chamber base 120, a second chamber wall 122, an air chamber arm 126, a needle 140, a needle chamber 142, and a base 150.

In one example, the first chamber 103 comprises a medicament chamber within the air removal apparatus 100 configured to hold medicament. As shown in FIG. 1, the space of the first chamber 103 can be defined by the area between the first chamber walls 104 and the chamber base 120. The first chamber walls 104 are coupled to the chamber base 120 and extend away from the chamber base 120, forming the space that defines the first chamber 103. Because the first chamber 103 can be defined by the area between the first chamber walls 104 and the chamber base 120, the first chamber 103 can be formed into several shapes. For example, if the first chamber walls 104 are cylindrical, the first chamber 103 will form a cylindrical shape. In some embodiments, the first chamber 103 can form other shapes. For example, the first chamber 103 can be triangular, rectangular, pentagonal, hexagonal, octagonal, and other geometric shapes. In some embodiments, the first chamber 103 can be open ended. In other embodiments, the first chamber 103 is sealed or closed off.

Medicament can be placed and stored within the first chamber 103. The medicament can occupy a part or all of the first chamber 103. In some embodiments, the medicament is located within a separate container, such as cassette or ampule. In some of these embodiments, the first chamber 103 can be designed to hold the cassette or other container within the first chamber 103. The first chamber 103 can be designed to hold the cassette, ampule or other container within the first chamber 103 by containing additional walls, fasteners, or other mechanical features, which can hold the cassette, ampule or other container in place within the first chamber 103.

In one example, the second chamber 102 comprises a dose chamber within the air removal apparatus 100 that can hold a dose of medicament. The second chamber 102 can be formed by the area between the chamber base 120, the second chamber walls 122, and the plunger 106. The second chamber walls 122 can be coupled to the chamber base 120 and extend away from the chamber base 120. The sides of the plunger 106 can contact the inner side of the second chamber walls 122, forming an airtight seal between the second chamber walls 122 and the sides of the plunger 106. This seal can be formed with a sealant or O-ring. Although the contact between the second chamber walls 122 and the plunger 106 can form an airtight seal, the plunger 106 can move along the second chamber walls 122 while maintaining the airtight seal.

The second chamber 102 can have a variable size or volume. The variable volume of the second chamber 102 can be caused by one of the parts forming the second chamber 102 moving. For example, the second chamber 102 can increase in volume as a result of the plunger 106 moving away from the chamber base 120 (as shown in the progression from FIGS. 1-3), or could decrease in volume as a result of the plunger 106 moving towards the chamber base 120.

The second chamber 102 can be formed into several shapes. For example, the second chamber 102 can form a cylindrical shape if the second chamber walls 122 are cylindrical. In some embodiments, the second chamber 102 can form other shapes. For example, the second chamber 102 can be triangular, rectangular, pentagonal, hexagonal, octagonal, and any other geometric shape.

In some embodiments, at least a portion of the second chamber walls 122 can be made from a gas-permeable material. For example, the second chamber walls 122 can be made from Polytetrafluoroethylene or other hydrophobic materials. This gas-permeable material can allow air to travel through the gas-permeable material while preventing any liquid or solid from passing therethrough. In some embodiments, the second chamber walls 122 are entirely made from the gas-permeable material. In other embodiments, a section or sections of the second chamber walls 122 are made from the gas-permeable material while the remainder of the second chamber walls 122 are made of a separate material or materials.

The plunger 106 can have one or more plunger arms 107 connected to the plunger 106. In some embodiments, the plunger 106 is connected to a single a plunger arm 107 that extends around the entire perimeter of the plunger 106, with the plunger arm 107 having a similar shape as the plunger 106. For example, the plunger arm 107 can be a cylinder that extends below the base of a circular-shaped plunger 106. In other embodiments, the plunger 106 is connected to two or more plunger arms 107, which are positioned around the bottom of the plunger 106. A plunger arm end 108 can be coupled to the plunger arm 107 at or near the end of the plunger arm 107. The plunger arm end 108 can have a flanged top and an angled bottom. In some embodiments, the plunger arm end 108 forms an entire ring around the bottom of the plunger arm 107. In other embodiments, the plunger arm end 108 is formed at one or more points along the plunger arm 107. In various embodiments, the plunger arms 107 and plunger arm ends 108 can be made from a flexible material, such as plastic, which allows the plunger arms 107 and plunger arm ends 108 to flex inwardly or outwardly.

Figure 2:
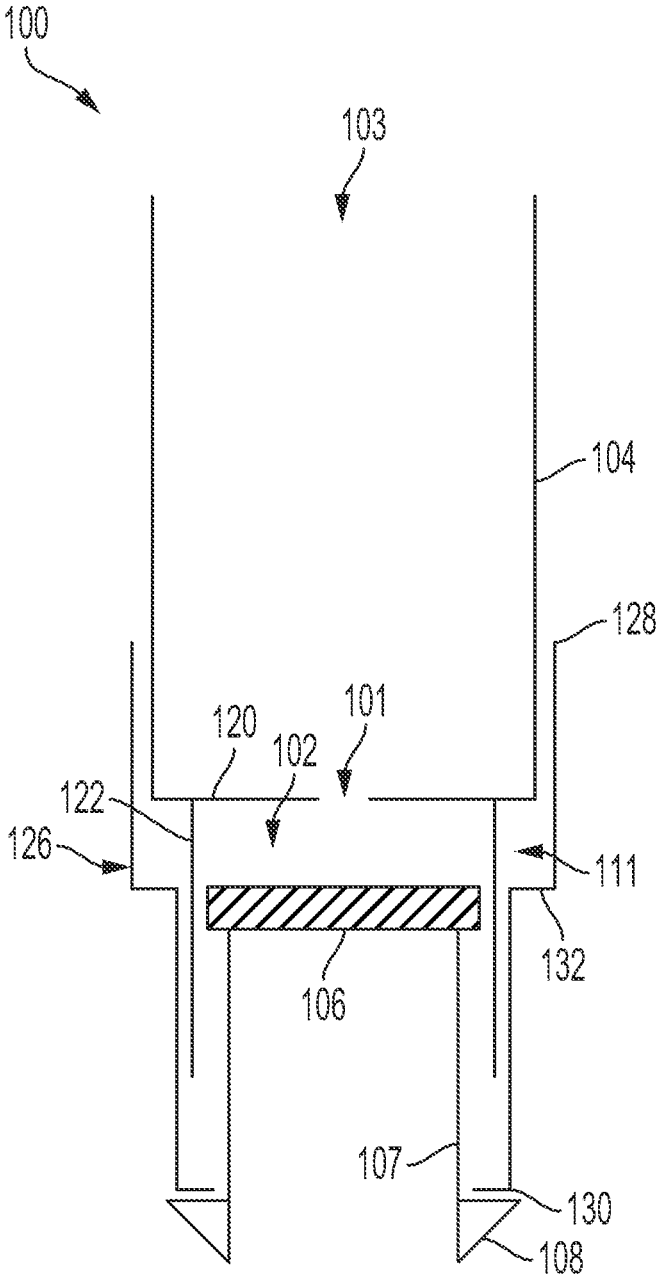
FIG. 2 is a side cross-sectional view schematically illustrating the example air removal apparatus of an autoinjector after an injection has been initiated.

As shown in FIG. 2, an air chamber 111 (also referred to as a third chamber) is a space within the air removal apparatus 100 configured to hold air from the second chamber 102. The air chamber 111 can be formed by the space between the first chamber 103, the second chamber 102, and the air chamber arm 126. In some embodiments, the air chamber 111 is formed by the space between the chamber base 120, the second chamber walls 122 and the air chamber arm 126.

The air chamber arm 126 can have an upper section 128 (e.g., a first end), a lower section 130 (e.g., a second end), and a shoulder 132 or bend. The shoulder 132 can be coupled to both the upper section 128 and the lower section 130. For example, the shoulder 132 may be formed between the upper section 128 and the lower section 130 such that the upper section 128 has a larger cross-sectional area than the lower section 130 and the upper section 128 and the lower section 130 can extend from the shoulder 132 in approximately opposite directions. In some embodiments, the lower section 130 can have a flange that extends inwardly towards the center of the air removal apparatus 100. The flange can be located at or near the end of the lower section 130. In some embodiments, the air chamber arm 126 does not have a lower section 130.

The upper section 128 of the air chamber arm 126 can connect to the first chamber 103 at the first chamber wall 104. In some embodiments, the upper section 128 of the air chamber arm 126 does not connect to the first chamber wall 104, but instead engages the first chamber wall 104 to permit slidable communication therebetween. In various embodiments, the upper section 128 forms an airtight seal with the first chamber wall 104. This airtight seal can be formed with a sealant or an O-ring. In various embodiments, in operation, the upper section 128 can move along the first chamber wall 104 in a direction toward the second end of the lower section 130, while maintaining the airtight seal. In some embodiments, the lower section 130 can be coupled to the plunger 106. The lower section 130 may be coupled to the plunger 106 at the plunger arm 107, the plunger arm end 108, or both. In various embodiments, the lower section 130 is not coupled to the plunger 106, but rather engages the plunger at the plunger arm 107 or plunger arm end 108. In other embodiments, the air chamber arm 126 does not engage and is not coupled to the plunger 106 in any capacity. In some embodiments, the coupling between the plunger 106 and the lower section 130 forms an airtight seal. This airtight seal can be formed with a sealant or an O-ring. In various embodiments, a part of the lower section 130 can contact the second chamber wall 122. The contact between lower section 130 and the second chamber wall 122 can form an airtight seal. This airtight seal can be formed with a sealant or an O-ring. In various embodiments, the lower section 130 can move along the second chamber wall 122 moving in a direction away from the chamber base 120 of the first chamber 103, while maintaining the airtight seal.

The air chamber 111 can have a variable size or volume resulting from the slidable communication between the air chamber arm 126 and the second chamber 102. The variable volume of the air chamber 111 can be increased or decreased based on a distance between shoulder 132 and chamber base 120. For example, the air chamber 111 can increase in volume as a result of an increase in the distance between the shoulder 132 and the chamber base 120. Alternatively, the air chamber 111 could decrease in volume as a result of a decrease in the distance between the shoulder 132 and the chamber base 120.

In various embodiments, the air removal apparatus 100 has a single air chamber arm 126 that surrounds a portion of the first chamber 103 and the second chamber 102. For example, the air chamber arm 126 can have a cylindrical profile which can fit around the first chamber walls 104, the second chamber walls 122, and the plunger arm 107. In other embodiments, the air removal apparatus 100 has two or more air chamber arms 126 which are installed at different points on the air removal apparatus 100.

The air removal apparatus 100 can include a needle 140 and a needle chamber 142. The needle 140 can be used to deliver the medicament from the second chamber 102 to the patient. The needle 140 can be formed from a variety of different gauges and can be a variety of lengths. The needle chamber 142 can hold the needle within the air removal apparatus 100.

Although not depicted in FIGS. 1-6, the air removal apparatus 100 can include other components that are commonly used with an autoinjector. For example, the air removal apparatus 100 can include a trigger, springs, filters, valves, a cover, a cassette, an ampule, and other autoinjector components.

The first chamber 103 can be in fluid communication with the second chamber 102. The hole 101 can be disposed through the chamber base 120, allowing any medicament, or other fluid, to travel between the first chamber 103 and the second chamber 102. In some embodiments, a valve is installed in the hole 101, which can restrict or permit any fluid to flow between the first chamber 103 and the second chamber 102. In some embodiments, the valve is a one-way valve which allows fluid to flow in only one direction. For example, the one-way valve can permit fluid to flow from the first chamber 103 to the second chamber 102, but prevent any fluid from flowing from the second chamber 102 into the first chamber 103. In various embodiments, a filter can be installed on the hole 101 or valve. The filter can be used to remove solid or unwanted particles from the medicament as the medicament flows into the second chamber 102.

The air chamber 111 can be in fluid communication with the second chamber 102. The air permeable portions of the second chamber walls 122 permit air to flow between the second chamber 102 and the air chamber 111. Although air can flow between the air chamber and the second chamber, any other fluids are prevented from flowing between the air chamber 111 and the second chamber 102.

In various embodiments, the air chamber arm 126 can move in tandem with the plunger 106. Because the air chamber arm 126 can be connected to the plunger 106, when one of these components moves, the other component must also move. For example, if the shoulder 132 of the air chamber arm 126 is advanced away from the chamber base 120, the flange of the lower section 130 can push the plunger arm end 108, causing the plunger 106 to move away from the chamber base 120. In some embodiments, the plunger 106 can move away from the chamber base 120, which in turn can cause the air chamber arm 126 to also move away from the chamber base 120. In some embodiments, the connection between plunger 106 and air chamber arm 126 can be severed, which can allow the plunger 106 and air chamber arm 126 to move independently from each other. In various embodiments, components from an autoinjector can interact with the air chamber arm 126 and plunger 106. For example, a spring or other biasing mechanism can be used to push down on the air chamber arm 126, causing the air chamber arm 126 and plunger 106 to move away from the chamber base 120. In other embodiments, a pin can be used to push down on the plunger, causing the plunger 106 and air chamber arm 126 to move away from the chamber base 120. In various embodiments the air chamber arm 126 and the plunger 106 operate independently of each other. For example, a biasing mechanism can cause the air chamber arm 126 to move while a separate biasing mechanism can cause the plunger 106 to move. In some embodiments, a single biasing mechanism connects to both the air chamber arm 126 and the plunger 106, causing each component to move when the biasing mechanism is activated.

The air removal apparatus 100 prevents air from being injected by creating a vacuum within the air chamber 111. Because the connection between the air chamber arm 126, first chamber walls 104, second chamber walls 122, and/or plunger arms 107 forms an airtight seal, any expansion within the air chamber 111 would result in a negative pressure forming within the air chamber 111. The resulting negative pressure would cause air to be drawn into the air chamber 111, which creates the vacuum. In various embodiments, the vacuum created in the air chamber 111 removes air in the second chamber 102. For example, the vacuum created in the air chamber 111 would draw air through the gas-permeable material of the second chamber wall 122, which would permit air removal from the second chamber 102. Once air is removed from the second chamber 102, the resulting injection will deliver a more accurate dose of medicament to the patient. In some embodiments, the vacuum created in the air chamber 111 does not remove all of the air from the second chamber 102, but instead reduces the amount of air within the second chamber 102. Any reduction of air within the second chamber 102 increases the likelihood that the ensuing injection will not contain air and that the medicament will not be displaced by air. In some embodiments, the air within the second chamber 102 can include any air bubbles within the medicament that is present within the second chamber 102. The air removal apparatus 100 can remove or trap air without the need for external equipment. Accordingly, the air removal apparatus 100 can remove or trap air within a closed system.

The change of volume of the air chamber 111 can affect the strength of a vacuum force that is created. Increasing the change of the volume of the air chamber 111 would increase the demand for air. As a result, increasing the change of volume would increase the negative pressure created in the air chamber 111 and vice versa. Accordingly, adjusting the distance between the shoulder 132 and the chamber base 120 can adjust the amount of negative pressure that is created within the air chamber 111. For example, increasing the distance between the shoulder 132 and the chamber base 120, increases the strength of the resulting vacuum such that the vacuum has a stronger force than a vacuum created by an air chamber 111 that had a smaller distance between the shoulder 132 and the chamber base 120. Furthermore, adjusting the size of the components that form the air chamber 111 can also affect when the vacuum force is created. For example, the width or diameter of the first chamber 103 and second chamber 102 can be designed so that the air chamber 111 does not increase in volume until the second chamber 102 is nearly full of medicament. As a result, the air chamber 111 would not create a vacuum force until the second chamber 102 is nearly full of medicament. Because the size and shape of the air chamber 111 can affect the resulting vacuum force, the size and shape of the parts that form the air chamber 111 can be adjusted in several ways to achieve different results. For example, in some embodiments, the first chamber 103 and the second chamber 102 are concentric, resulting in a vacuum force being applied equally around the second chamber 102. In other embodiments, the first chamber 103 and the second chamber 102 are offset, resulting in a vacuum force being applied more strongly to one section of the second chamber. In various embodiments, the first chamber 103 is wider, or has a larger circumference, than the second chamber 102. In other embodiments, the first chamber 103 is narrower, or has a smaller circumference, than the second chamber 102. In some embodiments, the shoulder 132 in air chamber arm 126 is slanted at angle or is curved. In some embodiments, the air chamber 111 is designed so as to increase its volume linearly. In other embodiments, the air chamber 111 is designed so as to increase its volume non-linearly. In various embodiments, the air chamber 111 is designed so as to increase its volume in a step-function manner. In some embodiments, the air chamber 111 is designed to decrease its volume, creating positive pressure within the air chamber 111. In other embodiments, the air chamber 111 is designed to both increase and decrease its volume.

The air removal apparatus 100 can be installed within an autoinjector. When installed within the autoinjector, the components of the air removal apparatus 100 can interact with components of the autoinjector. In some embodiments, the components of the autoinjector can interact with the air removal apparatus 100 in a manner that causes a vacuum to be formed within the air chamber 111. For example, the air removal apparatus 100 can be installed within an autoinjector such that the trigger that activates the injection process also activates the air removal process. In some of these examples, pressing the trigger of an autoinjector can cause a spring, or other biasing mechanism, to press down on the air chamber arm 126, which expands the air chamber 111 and creates the vacuum. In some embodiments, components from the air removal apparatus 100 can be replaced by components from the autoinjector, or removed entirely before being installed. For example, the first chamber could be replaced by an ampule.

With specific reference to the figures, FIGS. 1-6 illustrate the air removal apparatus 100 removing air from the second chamber 102 during an injection. In FIG. 1, the air removal apparatus 100 is positioned in a pre-injection state. During the pre-injection state, the medicament can be located entirely within the first chamber 103. The second chamber 102 can have a minimal volume, or no volume, as the plunger 106 is positioned near or against the chamber base 120. The air chamber 111 also can have a minimal volume, or no volume, as the shoulder 132 of the air chamber arm 126 is positioned near or against the chamber base 120. The lower section 130 of the air chamber arm 126 can be disconnected from the plunger 106 and positioned above the plunger arm end 108.

FIG. 2 illustrates the air removal apparatus 100 shortly after the injection process has begun. In FIG. 2, the shoulder 132 of the air chamber arm 126 is advanced in a direction away from the chamber base 120, which results in the air chamber arm 126 engaging the plunger arm end 108. The air chamber arm 126 engaging the plunger arm end 108 causes the plunger 106 to move away from the chamber base 120. As the plunger 106 moves away from the chamber base 120, the volume of the second chamber 102 expands. The expansion in the second chamber 102 draws medicament from the first chamber 103 through the one-way valve located at the hole 101. As medicament is drawn through the one-way valve, the medicament flows through a filter, which removes any solid particles from the medicament. Advancing the shoulder 132 of the air chamber arm 126 away from the chamber base 120 also results in the air chamber 111 expanding or increasing in volume. The expanding air chamber 111 creates a vacuum within the air chamber 111. The vacuum within the air chamber 111 draws air into the air chamber 111 from the second chamber 102. Air from the second chamber 102, including air within the medicament, flows through the gas-permeable material of the second chamber walls 122 and into the air chamber 111.

FIG. 3 illustrates the air removal apparatus 100 further along during the injection process illustrated in FIG. 2. In FIG. 3, the air chamber arm 126 has acted upon the plunger arm end 108 advancing the plunger 106 further away from the chamber base 120, which results in the second chamber 102 volume increasing. Because the distance between the shoulder 132 and the chamber base 120 has increased, the volume of the air chamber 111 has also increased. The expanding volume of the air chamber 111 continues to create a vacuum within the air chamber 111. Accordingly, the air chamber 111 continues to draw air into the air chamber 111 from the second chamber 102 throughout the injection process. At this stage of injection, the air chamber arm 126 is positioned at or near the fully extended position with a maximum distance between the shoulder 132 the chamber base 120. In some embodiments, the air chamber arms 126 can be prevented from extending entirely below the chamber base 120. For example, a stop, or base 150, can be installed at the bottom of the air removal apparatus 100, which can engage the shoulder 132 and prevent the plunger arms 107 from moving any lower.

FIG. 4 illustrates the air removal apparatus 100 with a needle 140 and needle chamber 142 while the air removal apparatus 100 is in an extended position. In some embodiments, the needle 140 and the needle chamber 142 can be installed within the air removal apparatus 100 so that the needle 140 and needle chamber 142 are not engaging the plunger 106. For example, the needle 140 and needle chamber 142 can rest against a base 150.

FIG. 5 illustrates the air removal apparatus 100 before the medicament is injected in the patient. The needle 140 has pierced the plunger 106, which puts the needle 140 and the second chamber 102 in fluid communication. With needle 140 in fluid communication with the second chamber 102, medicament from the second chamber 102 can be delivered to the patient. In some embodiments, the plunger arms 107 can be pinched inwardly. For example, the base 150 can engage the angled plunger arm end 108, causing the plunger arm 107 to pinch inwardly. Pinching the plunger arms 107 inwardly disengages the plunger arm ends 108 from the air chamber arms 126, which allows for the plunger 106 and air chamber arms 126 to move independently from each other.

FIG. 6 illustrates the air removal apparatus 100 after the medicament is injected in the patient. The plunger 106 is retracted and is pressing against the chamber base 120. Accordingly, the volume of the second chamber 102 is minimized. In some embodiments, the volume of second chamber 102 is nonexistent or substantially nonexistent. Although the volume of the second chamber 102 has been reduced, the volume of the air chamber 111 remains in its expanded positioning. The air chamber 111 remaining in the expanded position ensures that any air removed from the second chamber 102 stays within the air chamber 111.

In various embodiments, the air removal apparatus 100 can be used independently from an autoinjector. For example, the air removal apparatus 100 can be used to remove or trap air from other closed systems, or to remove air from a system without using an external vacuum source. In some embodiments, the air removal apparatus 100 can be modified so that the air removal apparatus 100 can interact with systems that are different from an autoinjector. The air removal apparatus 100 can be modified by removing, adding, or changing components.

Figure 7:
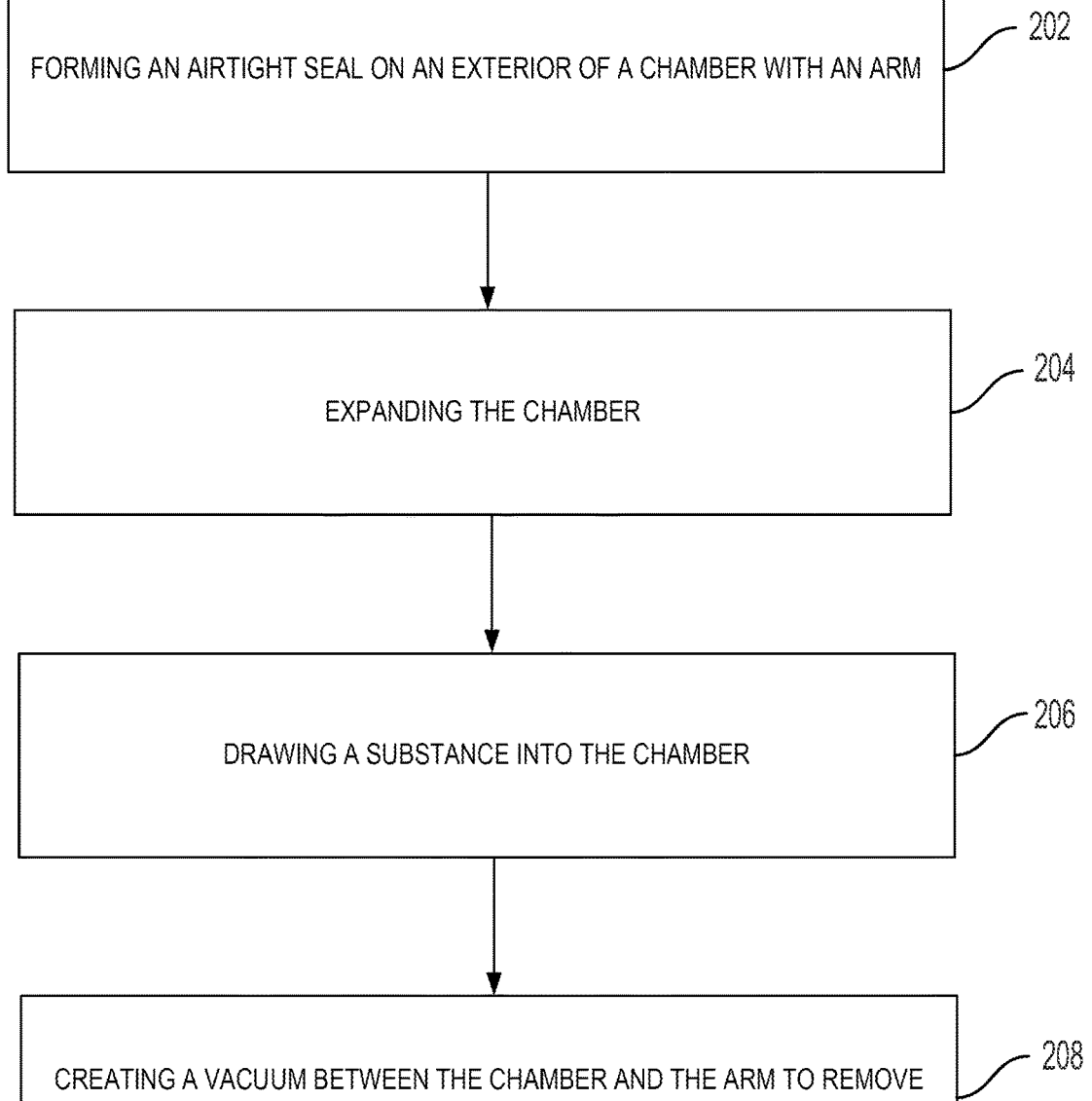
FIG. 7 is a flowchart illustrating an example method according to an example embodiment.

FIG. 7 is a block diagram of an example method of removing a gas from an autoinjector. Method 200 shown in FIG. 7 presents an embodiment of a method that could be used by the air removal apparatus 100 as described in FIGS. 1-6, as examples. Method 200 may include one or more operations, functions, or actions as illustrated by one or more of blocks 202-208. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 200 and other processes and methods disclosed herein, the block diagram shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

Initially, at block 202, the method 200 includes forming an airtight seal on an exterior of a chamber with an arm. At block 204, the method 200 includes expanding the chamber.

At block 206, the method 200 includes drawing a substance into the chamber. At block 208, the method 200 includes creating a vacuum between the chamber and the arm to remove the gas from the chamber.

Figure 8:
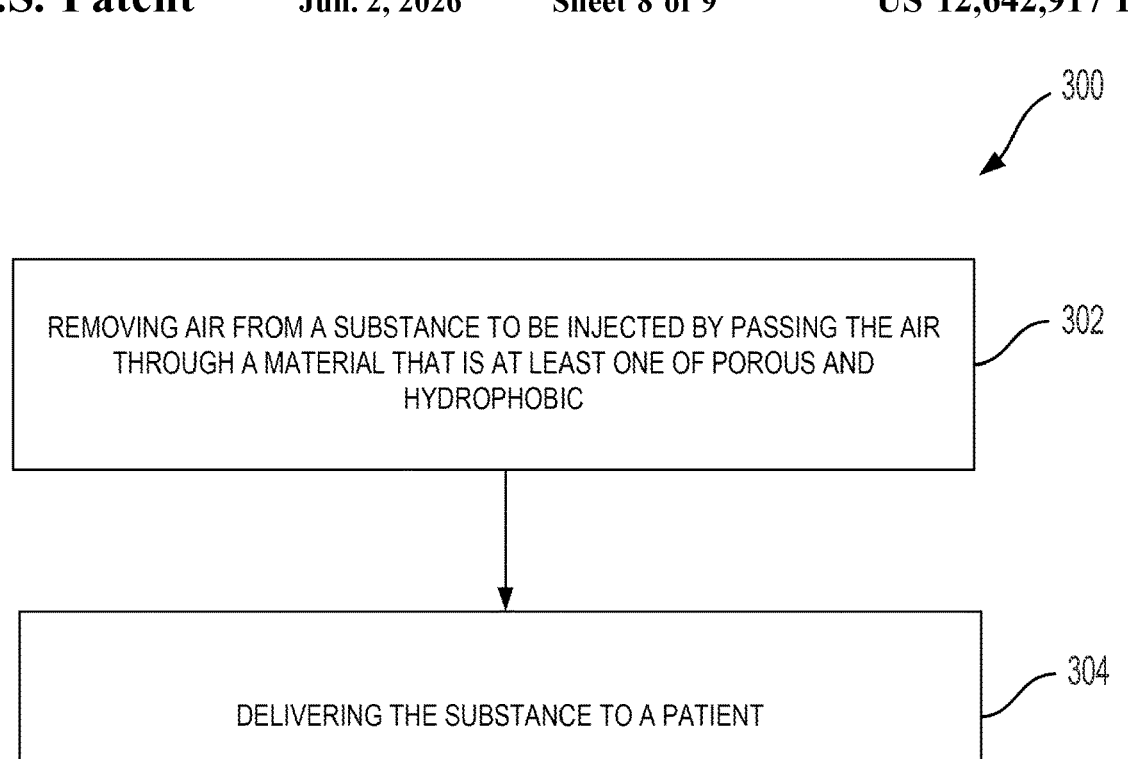
FIG. 8 is a flowchart illustrating another example method according to an example embodiment.

FIG. 8 is a block diagram of an example method of removing a gas from an autoinjector. Method 300 shown in FIG. 8 presents an embodiment of a method that could be used by the air removal apparatus 100 as described in FIGS. 1-6, as examples. Method 300 may include one or more operations, functions, or actions as illustrated by one or more of blocks 302-304. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

Initially, at block 302, the method 300 includes removing air from a substance to be injected by passing the air through a material that is at least one of porous and hydrophobic. At block 304, the method 300 includes delivering the substance to a patient.

Figure 9:
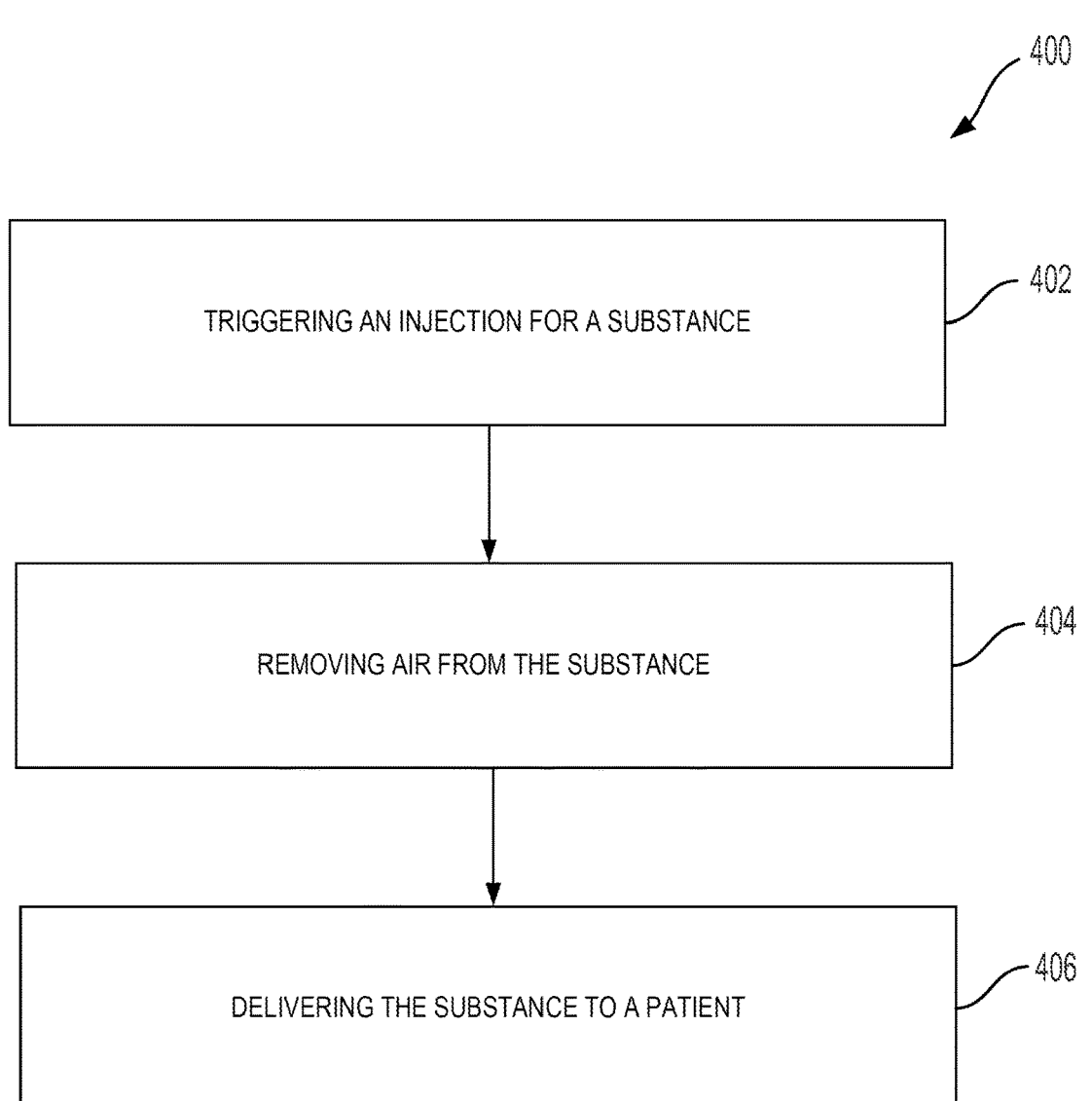
FIG. 9 is a flowchart illustrating another example method according to an example embodiment.

FIG. 9 is a block diagram of an example method of removing a gas from an autoinjector. Method 400 shown in FIG. 9 presents an embodiment of a method that could be used by the air removal apparatus 100 as described in FIGS. 1-6, as examples. Method 400 may include one or more operations, functions, or actions as illustrated by one or more of blocks 402-406. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

Initially, at block 402, the method 400 includes triggering an injection for a substance. At block 404, the method 400 includes removing air from the substance. At block 406, the method 400 includes delivering the substance to a patient. In some embodiments, the method 400 further includes partially or fully filling a second chamber 102 with the substance prior to removing air from the substance.

The injection process of an autoinjector can be triggered in several different ways. For example, a user can press a trigger on an autoinjector, which starts the injection process. The second chamber 102 can be partially or fully filled in a variety of different ways. For example, a biasing mechanism can cause the second chamber 102 to expand, which draws the substance (e.g., a medicament) into the second chamber 102. In some embodiments, the second chamber 102 can be prefilled with a medicament. All or some of the air can be removed from the medicament by creating a vacuum within an air chamber 111. The vacuum within the air chamber 111 can draw air through the gas-permeable material of the second chamber walls 122, causing air to be removed from the medicament disposed within the second chamber 102. The remaining medicament can be delivered to a patient by using a needle 140 to transfer the medicament from the autoinjector and to the patient.

After the autoinjector is triggered a biasing mechanism can act upon air chamber arms 126, causing the volume of the air chamber 111 and the volume of the second chamber 102 to expand. As the volume of the second chamber 102 expands, medicament flows from the first chamber 103 into the second chamber 102. The medicament can be filtered before entering the second chamber 102 so as to remove any solid or unwanted particles from entering into the second chamber 102. The expanding volume of the air chamber 111 creates negative pressure within the air chamber 111, causing a vacuum to form within the air chamber 111. The vacuum created within the air chamber 111 draws any air, or some of the air, from the medicament in second chamber 102 into the air chamber 111 and traps the air within the air chamber 111. Once the volume of the second chamber 102 fully expands, the plunger arms 107 disengage from the air chamber arm 126 and a needle 140 pierces the plunger 106. Next, the medicament is delivered to the patient and the plunger 106 is retracted. In some embodiments of an injection process, an autoinjector is triggered. After, or before, the injection process for an autoinjector is triggered, the first chamber 103 is partially or fully filled with a medicament. After the autoinjector is triggered, any air, or some of the air, is drawn out of the medicament. Next, the medicament is delivered to the patient.

While certain embodiments have been described, these embodiments have been presented by way of example only, and are not intended to limit the scope of the disclosure. Indeed, the novel apparatus, methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present disclosure is defined only by reference to the appended claims. In some embodiments, the de-bubbler system is used separately from an autoinjector system. In some embodiments, a closed system de-bubbler is provided in which no external vacuum source is needed. Upon activation, a new chamber is formed, creating a negative pressure that acts as the vacuum source.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y. or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" and "about parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

We claim:

1. An autoinjector comprising:

a first chamber configured to hold a substance, the first chamber including a base;

a second chamber coupled to the first chamber, the second chamber being defined by the base of the first chamber, a first wall, and a plunger, wherein the second chamber is configured to increase in volume in response to the plunger moving away from the base of the first chamber; and a hole disposed through the base of the first chamber such that the hole is in fluid communication with the first chamber and the second chamber, wherein the first wall has a gas-permeable portion, and wherein increasing the volume of the second chamber draws the substance from the first chamber into the second chamber and expels a gas out of the second chamber and through the gas-permeable portion, wherein the autoinjector further comprises an arm including a first end and a second end opposite the first end, the arm being coupled to the first chamber at the first end and the second chamber at the second end such that the arm forms an airtight seal between the arm and the first chamber and the second chamber, the arm being configured to move with the plunger.

2. The autoinjector of claim 1, further comprising a third chamber, the third chamber being defined by a space between the arm, the first chamber, and the second chamber, the third chamber is being configured to increase in volume in response to the plunger moving away from the base of the first chamber.

3. The autoinjector of claim 2, wherein increasing the volume of the third chamber creates a vacuum within the third chamber.

4. The autoinjector of claim 1, further comprising a needle coupled to the plunger such that the needle is in fluid communication with the second chamber.

5. The autoinjector of claim 1, wherein the second chamber is narrower than the first chamber.

6. The autoinjector of claim 1, wherein the hole is a one-way valve.

7. The autoinjector of claim 1, wherein the first chamber and the second chamber are concentric.

8. The autoinjector of claim 1, wherein the second chamber is cylindrical.

* * * * *